United States Patent
Shrairman et al.

(10) Patent No.: US 6,546,134 B1
(45) Date of Patent: Apr. 8, 2003

(54) SYSTEM FOR ASSESSMENT OF FINE MOTOR CONTROL IN HUMANS

(76) Inventors: Ruth Shrairman, 7783 Cornwall Cir., Boulder, CO (US) 80301; Alexander Landau, 7783 Cornwall Cir., Boulder, CO (US) 80301

(*) Notice: Subject to any disclaimer, the term of this patent is extended or adjusted under 35 U.S.C. 154(b) by 0 days.

(21) Appl. No.: 09/535,777

(22) Filed: Mar. 28, 2000

Related U.S. Application Data (60) Provisional application No. 60/126,762, filed on Mar. 29, 1999.

(51) Int. Cl.[7] ............... G06K 9/00; G06K 9/18; G06K 9/56; A61B 5/00; G09B 19/00

(52) U.S. Cl. ............ 382/186; 382/120; 382/122; 382/181; 382/187; 382/205; 382/278; 382/306; 73/865.4; 434/155

(58) Field of Search ............... 382/107, 115, 382/116, 119, 120–122, 181, 185, 186, 187, 188, 189, 190, 202, 205, 209, 218, 219, 278, 305, 306, 313; 73/865.4; 178/18.01, 18.03; 340/5.52, 5.53; 434/155; 707/1; 902/3

(56) References Cited

U.S. PATENT DOCUMENTS

| | | | |
|---|---|---|---|
| 4,024,500 A | * 5/1977 | Herbst et al. | 382/178 |
| 4,040,012 A | * 8/1977 | Crane et al. | 382/121 |
| 4,562,592 A | * 12/1985 | Chainer et al. | 382/120 |
| 4,736,445 A | * 4/1988 | Gundersen | 382/120 |
| 5,022,086 A | * 6/1991 | Crane et al. | 382/121 |
| 5,040,222 A | * 8/1991 | Muroya | 382/123 |
| 5,202,930 A | * 4/1993 | Livshitz et al. | 382/122 |
| 5,802,200 A | * 9/1998 | Wirtz | 382/119 |
| 6,148,093 A | * 11/2000 | McConnell et al. | 382/119 |

OTHER PUBLICATIONS

Plamondon "The handwritten signature as a biometric identifier: psychophysical model and system design", IEEE, pp. 23–27, 1995.*

Alimi "A neuro–fuzzy approach to recognize arabic handwritten characters", IEEE, pp. 1397–1400, 1997.*

* cited by examiner

*Primary Examiner*—Andrew W. Johns
*Assistant Examiner*—Daniel G. Mariam
(74) *Attorney, Agent, or Firm*—Donald W. Margolis

(57) ABSTRACT

A biometric machine method for instantaneous assessment of the fine motor control of a human individual through analysis of that individual's handwriting dynamics in which the dynamic data concerning forces, accelerations, and the like, of a scriber, is collected during the process of cursive writing. The criteria of stability, smoothness and synchronization of the writer's motion are returned by the system as quantifying measures of the neurological function. The method processes behavioral random signals with application of the correlation function analysis to the handwriting dynamic signals. In one embodiment, the system includes an instrumented pen connected to a computer, power supply, and analog-to-digital converter, and with the handwriting samples provided on any writing surface. In a second embodiment, the system comprises an instrumental digital tablet having an active area and non-instrumented scriber with the handwriting samples provided on the active area of the grid. The method is simple and not invasive. The analysis takes less than a minute to return the numerical criteria scores and graphical displays showing stability of the handwriting strokes and the characteristics of the phase distortions in reproducing cursive samples. The invention can be applied for monitoring patients with neurological disorders, monitoring people with alcohol/drug abuse problems, detection of fine motor control deterioration as a result of exposure to toxic materials, and testing the efficacy of countermeasures to improve impaired fine motor control functions.

10 Claims, 5 Drawing Sheets

Schematic diagram of the "window-shadow" mechanism (a)  (b)

SYSTEM FOR ASSESSMENT OF FINE MOTOR CONTROL IN HUMANS

RELATED APPLICATIONS

This application claims the filing date of U.S. Provisional Patent Application No. 60/126,762 for System For Assessment of Fine Motor Control of Humans Using Handwriting Dynamics filed March 29, 1999.

BACKGROUND OF THE INVENTION a) Field of the Invention

This invention relates to a biometric machine method for quantitative assessment of fine motor control of human individuals through the monitoring of changes in cursive writing dynamics. Such quantitative assessment uses Correlation Function Analysis of handwriting dynamic signals, such as acceleration and pressure, in time domain, and returns values of criteria for stability, smoothness and synchronization of handwriting motions.

b) Description of the Prior Art

It has been very difficult to identify individuals with unset Parkinson's and other neurological diseases because of subtlety of the early symptoms It is therefore difficult to identify and adequately characterize the unset of fine motor control deficiencies in such individuals. It has also been difficult to assess impairment or impediment in fine motor control due to the influence of alcohol and drug substances, or from environmentally caused distress. Handwriting is a complex cognitive motor skill. Since handwriting is usually a well-learned skill that is generally used on a daily basis, the motor behavioral aspects of handwriting are theoretically interesting and practically important particularly in the early identification and assessment of fine motor control impairment as a result of the above-mentioned problem. Thus, research based on the changes in handwriting dynamics have been considered in an effort to better understand, identify, and assess human fine motor control. In the recent past there has been a growing interest in research in fine motor control of humans through analysis of handwriting dynamics. Several publications in the field of Neurology represent this trend. For example, David Margolin and Alan Wing, in their paper "*Agraphia and Micrographia: Clinical Manifestations of Motor Programming and Performance Disorders*" published in Acta Psychologica, 1983, presented the results of research of acquired disorders of handwriting. They compared acquired agraphia due to cerebrovascular accident to micrographia produced by the Parkinsonian patients. They stated, "existing reports of apraxic agraphia . . . do not provide much information about handwriting control from an information processing standpoint, although they can be useful in determining the anatomical localization of handwriting control. Overall, the reported cases of apraxic agraphia indicate that handwriting can be disrupted without affecting other motor skills." Parkinsonism, on the contrary, "affects all voluntary movements, but handwriting appears to be particularly vulnerable, in that it is frequently the first manifestation of this disease." And they conclude "if handwriting is indeed sensitive to disturbances of the extrapyramidal motor system then a quantitative analysis of writing could serve as a useful tool in evaluating diseases which affect this system and provide insights into dynamics behind these handwriting changes." The present invention provides such new channels of information about motor control of handwriting and will shed light on the complex mechanisms of fine motor control.

In the research of handwriting generation by R. Plamondon published in Acta Psychologica 82 (1993), the author states "strokes must be superimposed to generate fluent handwriting. This is in accordance with a basic psychophysical phenomenon often reported in motor control: the handwriting generation process, like many other types of movements, is not exclusively sequential, and very often advanced preparation of the forthcoming stroke is done in parallel with the execution of the actual stroke. . . . In other words, the basic strokes are hidden in the signal." In conclusion, Plamondon suggests the method to extract strokes by performing "an analysis-by-synthesis experiment, with the help of the proper impulse response for each stroke" and the use of quite complicated models of reconstructing the curvilinear velocity profiles defined by a log-normal equations. However, Plamondon presents a method for mathematical modeling of individual strokes and fails to teach a system for analysis of sequences of strokes. The extraction of single strikes and their modeling and analysis, as proposed by Plamondon, would result in loosing important information about behavior of strokes in their sequence. In addition to that, identification and high precision modeling of individual strokes represents very difficult and even unfeasible task because of greatest complexity of each handwriting movement where numerous elements of the central control and neuromuscular systems are involved in their performance. The present invention teaches a new analysis of the handwriting dynamic signals as indivisible collections of strokes intermittent with time distortions, contrary to considering individual strokes.

E. Parkins in his article "*Cerebellum and Cerebrum in Adaptive Control and Cognition: a Review*" published in Biological Cybernetics, 77 (1997), explores the relative roles of the cerebrum and cerebellum in adaptive control. Parkins makes an interesting observation: "Voluntary movements may first be performed and controlled by relying on feedback from sensory organs, but after some practice the same movement will be performed without feedback, the movement being performed more quickly and more automatically with less conscious effort. Here, practice converts the mode of voluntary movement from feedback to feed forward. The cerebellum operating as an adaptive feedforward system may be inserted in parallel to the cerebral cortex operating as an executive feedback-control system." The present invention, through measurement and assessment of handwriting dynamics representing both automatic, such as signature, and cognitively controlled cursive writing, such as "llll", "lmlm", "lele", etc., provides valuable and previously unavailable information about the role and interplay of cerebellum and cerebrum in adaptive motor control and cognition.

Between 1994 and 1997, a joint European project, MIAMI(Multimodal Integration for Advanced Multimedia Interfaces) for the universities of The Netherlands, Germany, Denmark, and Italy was conducted for extensive research of human handwriting. The report of MIAMI resents the following observation: "Contrary to speech, cursive handwriting is not an innate neural function, and must be trained over several years. During the training process, handwriting evolves from a slow feedback process involving active attention and eye-hand coordination to a fast automatic and ballistic process. The atomic movement unit in cursive handwriting is a stroke, which is a movement trajectory bounded by two points of high curvature and a corresponding dip in the tangential movement velocity. The typical modal stroke duration is of the order of 100 msec, and varies less for increased movement amplitudes than one would expect. For a large range, writers exert an increased force in order to maintain a preferred rhythm of movement.

Once "fired" cortically, such a stroke cannot be corrected by visual feedback".

Some early publications in the field of physiology also represent interest for the present invention. In 1864, Russian physiologist K. I. Barr published his work in which he first introduced the concept of "biological quantum of time" which was further developed by German researchers J. V. Uexkull and G. Kriszat, who called it "physiological moment" in their paper "Streifzuge durch die Umwelten von Tieren und Menschen", 1970. It is very plausible to assume that the stroke, the atomic movement unit in cursive handwriting, is a spatial representation of the biological quantum. The biological quantum of time is estimated to be 100 to 180 msec. In addition to the literature, several devices have been developed to measure tremor. The primary known devices include:

1. Potentiometers to indicate motion of an extremity. They use a mechanical linkage, similar to an articulated dentists' drill arm with a potentiometer at each joint. However, such linkages very greatly restrict the physical motion of the extremity, and can create backlash and hysteresis.
2. Electromyographic (EMG) surface electrodes attached to the skin are used to . . . assess tremor in the muscles during cursive writing. The problem with EMG is that signals that are indicative of tremor are obscured by remote muscle activity and electrical interference. In addition, the EMG equipment is cumbersome, not easily manageable and not portable.
3. Accelerometers to record acceleration of the upper extremity movement, and to compute the velocity of the extremity as its first integration and the displacement as its second integration. Accelerometers are mounted on a Lucite board strapped to the hand that is supported by a second board, forming a sandwich with the hand between the boards. In the implementation used, one accelerometer could not distinguish the actual tremor from the perceived motion, since a slight reorientation of the sensitive axis of the accelerometer with respect to the earth's gravitation field can cause it to record an acceleration variation without any actual tremor. Due to any orientation shifts and bias error, which represents the non-zero output when there is no input, just the first integration of the accelerometer's output to obtain the velocity of the motion would generate ample error to make use of accelerometers for measurement of motion impractical.
4. Gyroscopes sense the angular rate as a function of time and frequency. By utilizing one or more small solid-state gyroscopes, which are attached to hands, feet, or head, physical motion can be quantified. However, the gyroscope system is limited to measuring the angle variations of motion only, and like all previously mentioned devices requires attachment to the subject's body.
5. Applicants, Alexander Livshitz, now known as Alexander Landau, and Ruth Shraiman have been granted U.S. Pat. No. 5,202,930 for High Precision On-Line Dynamic Signature Verification System. It teaches a machine method for electronic on-line signature verification based on comparison of the dynamics of sample and reference data. Multi-dimensional cross-correlation function analysis is applied, with use of sliding window mechanism for mapping phase coincident regions of the reference and to-be-verified signals. By establishing high level of statistical similarity between the said signals, the method provides means for authentication of an individual in a variety of security applications, such as computer networks access, credit card authentication, electronic voting, and the like.

However, none of these systems or literature teach a system for a rapid, non-intrusive, reliable, and low-cost system for quantifying fine neuromuscular performance and fine motor control skills of human individuals using cursive writing and minimal equipment.

SUMMARY OF THE INVENTION

It is therefore an object of the present invention to provide a rapid, reliable, non-intrusive, and low-cost system for quantifying fine neuromuscular performance and fine motor control skills of human individuals using cursive writing and minimal equipment.

In addition, it is an object of the present invention to provide a method for instantaneous, within the subject evaluation of fine motor control, without the need to have reference data for that individual.

The present invention addresses the problem of quantifying assessment fine motor control skills in human individuals. As detailed below, the method applies correlation function analysis for instantaneous, within the subject comparison of behavioral random signals of cursive handwriting dynamics within the human individual, without the need to have reference handwriting dynamic data from that individual, and use that data to derive the measures of stability, smoothness and synchronization of the hand motions. Those measures of hand motion are compared against the data values established across the healthy population of humans, as represented by their mean and standard deviation, and using the comparative data to assess any deterioration in fine motor performance of an individual. This is accomplished,. as taught by the present invention by providing a method, apparatus and machine method for instantaneous assessment of fine motor control of humans through analysis of cursive handwriting dynamics by using the application of correlation analysis for comparison of random signals that are represented by repetitively produced cursive handwriting samples by an individual.. In the practice of the present invention, the dynamic data concerning forces, accelerations, and the like, of a scriber, such as a pen, are collected during the process of cursive writing. The criteria of stability, smoothness, and synchronization of the cursive writing motion of the individual are returned by the system as quantifying measures of the neurological function of that individual. In the practice of the present invention, a cursive handwriting pattern is considered as a sequence of ballistic strokes. Replication of a pattern may be generated from a single, high-level memory representation, acting as a motor program. The displacement of the scriber is a result of a natural double integration of the acceleration variations in time. As such, the scriber displacement does not represent the high frequency part of the initial signal spectrum suppressed by the integration process, and it cannot be expected to obtain critical first-hand information about fine motor control by measuring second-hand effects. That is why the method of the present invention is based on analysis of accelerations and forces as the source of complete and substantial information about handwriting dynamics. This approach allows detection of deterioration in an individual's cursive handwriting, even in cases of small, normally invisible deviations in handwriting.

The method takes as an input handwriting dynamic signals gathered on a millisecond time scale, and returns, as an output, very precise measurements of stability, smoothness, and synchronization of the handwriting movements. The method of the present invention focuses on how a person writes as opposed to how writing looks. The system translates the writing dynamics of acceleration and pressure into complex signals, with each signal represented by as many as 1000 data points. Then, as a key part of the signal processing, any two writing signals, which represent repeated realizations of the same handwriting samples are compared in order to establish statistical similarity of the signals. The samples might be, any sequence of cursive writing, including signatures and hand-drawn symbols.

The method uses a new approach for Correlation Function Analysis applied to behavioral signals, such as handwriting dynamics. The behavioral signals of cursive writing are not stable by nature, and relate to "non-stationary" signals, and subsequently are intractable for classical correlation function analysis. One key feature of the present invention relies on the discovery that those behavioral signals are stationary for a very short period of time, about 100 milliseconds, the order of a biological quantum, and that the quanta are intermittent with random length intervals. Those stationary signal segments may be considered as realizations of the preprocessed brain program of the individual implemented by nerve impulse propagation and by muscle contraction. The random intervals between those segments are understood to represent variations in the nerve stream propagation and in muscle contraction between the biological quanta. In other words, statistical stationarity has been found to have a granular character, and the information about fine motor skill is represented by the assembly of "granules", as well as by the manner in which the intervals between granules occur.

In order to maintain the fine motor control assessments of the present invention with high accuracy, a "window-shadow" mechanism, as detailed below, is used to discriminate granules against the intervals between them. Then the method determines the level of cross-correlation between quasi-stationary signals consisting of those granules glued with one another, as well as analyzes the behavior of the intervals in order to characterize stability, smoothness and synchronization of handwriting movements.

The present invention also teaches a biometric machine method for instantaneous assessment of the fine motor control of a human individual through analysis of the handwriting dynamics of that individual using a scriber. A computer collects the dynamic data concerning forces, accelerations, and other properties of the scriber during the process of cursive writing. The criteria of stability, smoothness and synchronization of the hand motion of the writer are analyzed by a computer as quantifying measures of the neurological function of the human individual. The method processes behavioral random signals by the application of the Correlation Function Analysis to the handwriting dynamic signals. In addition, the frequency analysis of the signals is performed using Fourier analysis.

In one machine method embodiment, the system of the present invention includes a small, lightweight instrumented scriber, such as a pen, connected to a computer, power supply, and an analog-to-digital converter of handwriting samples made on any writing surface. In a second embodiment, the system comprises a digital tablet having an active grid surface and a non-instrumented scriber, with the handwriting samples collected on the active surface area of the grid. The method is simple and not invasive. The analysis takes less than a minute to return the numerical criteria scores and graphical-displays showing stability of the handwriting strokes and the characteristics of the phase-distortions in reproducing cursive samples.

The machine method can be implemented as a stationary system with use of a desktop computer and as a portable system with the use of a portable computer. The present invention can be used for early diagnostics of Parkinson's disease and other neurological disorders, for monitoring individuals with known neurological disorders in order to determine that persons response to treatment, for expediting clinical trials of neurological pharmaceuticals, for monitoring people with alcohol/drug abuse problems, for the detection of fine motor control deterioration as a result of exposure to toxic environmental materials, or for testing the efficacy of countermeasures to improve impaired fine motor control functions.

The system of the present invention makes assessment of fine motor control, through measurement and analysis of handwriting dynamics representing both ballistic patterns, such as signature, and cognitively controlled cursive patterns of cursive patterns. Such ballistic and cognitively controlled cursive patterns have been found to provide precious and previously unavailable information about the role and interplay of cerebellum and cerebrum in adaptive control and cognition. It is in this vein that the method of the present invention, by measuring handwriting disturbances, provides useful information for the complex mechanisms of fine motor control, and provides information concerning human individuals with neurological disorders, in cases of drug/alcohol impairment and environmental distress. The method also allows evaluation of the effectiveness of therapeutic treatment of the neurological patients, and the design of adequate training protocols for learning disability problems.

These and other objects of the present invention will become apparent to those skilled in the art from the following detailed description, showing the contemplated invention as herein described, and more particularly defined by the appended claims, it being understood that changes to the precise embodiments of the herein disclosed invention are meant to be included as coming within the scope of the claims, except as they may be precluded by the prior art.

BRIEF DESCRIPTION OF THE DRAWINGS

The accompanying drawings illustrate complete preferred embodiments of the present invention according to the best modes presently devised for the practical application of the principal thereof, and in which:

FIGS. 3, *a* and *b* is a diagram showing phase delays for a person having no neurological disorder (a) and phase delays for a patient with Parkinson's disease (b);

FIGS. 4, *a* and *b* shows pictorial representation of handwriting samples of a Parkinson's disease patient before (a) and 40 minutes after taking L-dopa medication (b);

FIGS. 5, *a* and *b* shows computer screens with displays of correlation function and the phase shift variations in time as a part of the handwriting dynamic analysis for the same Parkinson's disease patient before (a) and after (b) taking L-dopa medication;

FIGS. 6, a and b shows the graphs for phase distortions, before (a) and after (b) taking L-dopa medication for a patient with advanced Parkinson's disease.

DETAILED DESCRIPTION OF THE INVENTION

The present invention proposes a method by which digital signals of the handwriting dynamics that belong to the class of random behavioral signals can be analyzed to give unique characteristics of the person's fine motor control.

In Communication Theory, the statistical similarity of stationary signals is measured by the maximum of the cross-correlation function between compared signals in time. This approach is optimal in the sense that noise components of signals are filtered out nearly completely for most of the existing kinds of noise provided sufficient length of the signals.

The main problem in establishing statistical similarity between behavioral signals is their non-stationarity. This makes the problem intractable using of the classical statistical processing of signals. The innovation presents an approach that attacks this problem. As a result, three criteria for measurement of stability, smoothness and synchronization of the handwriting dynamics signals have been derived.
Stability Criterion, $Cr_1$ For the time interval 2T, the cross correlation function R ($\tau$) is estimated by the following formula $$R(\tau) \approx \frac{1}{2T} \int_{-T}^{+T} f_1(t) \cdot f_2(t+\tau) dt$$

where $f_1(t)$ and $f_2(t)$ are time functions representing two centralized signals of handwriting dynamics to be compared, and $\tau$ is "lag" time.

Prior to the correlation function analysis for evaluating signal matching, a pair of the compared signals is preprocessed to eliminate time or phase distortions, so that the signals can be compared as though both sets of data were stationary signals. A "window-shadow" mechanism was introduced in order to identify phase distortions and to exclude them from the correlation function computation (see FIG. 1). This mechanism is implemented by applying cross-correlation analysis to sequential, relatively small pieces of a given signal, called "windows", and finding, over the predetermined interval of search, the corresponding pieces of another signal in the compared pair, called "shadows". Thus, the mapping between phase coincident regions of the compared signals is established, and the correlation function for the resulting "quasi-stationary" signals is computed. The value of the maximum of the cross correlation function calculated for the compared signals along any chosen axis defines the Stability Criterion for X, Y, and Z axis, respectively.

Smoothness Criterion, $Cr_2$ and Synchronization Criterion, $Cr_3$

The difference in positioning of a "window" and its "shadow" in time scale is called "shift". The shifts define phase delays, or distortions. It appears that the relative positioning of windows and their shadows give additional and very rich information about distribution of the phase distortions in an individual's handwriting dynamics. Analysis of phase distortions allowed us to derive another two powerful criteria, to determine smoothness and synchronization of the person's handwriting movements.

Provided the window-shadow shifts yield to the Normal distribution, let $sigma_{sh}$ denote a dispersion of the shifts distribution. Then, for any chosen axis X, Y, or Z, the portion of the first order differences for window-shadow shifts taken in the predetermined intervals, normally about 15 msec, of the window-shadow shifts distribution defines Criterion II ($Cr_2$) for the corresponding axis.* It characterizes smoothness of hand movement along this axis.

The differences in positioning of windows and their shadows along one axis are compared with their counterparts along another axis. Provided the differences of shifts between two chosen for comparison axes yield to the Normal distribution, let sigma denote a dispersion of the shift-differences distribution. Then the portion of the differences between window-shadow shifts for two chosen axes taken within predetermined interval, normally about 15 msec, defines Criterion III ($Cr_3$) for this pair of axes. This criterion characterizes inconsistencies in window-shadow shifts along the two axes, i.e., it characterizes synchronization or de-synchronization of handwriting movements along the two chosen axes, for instance X and Y.

Figure 1:
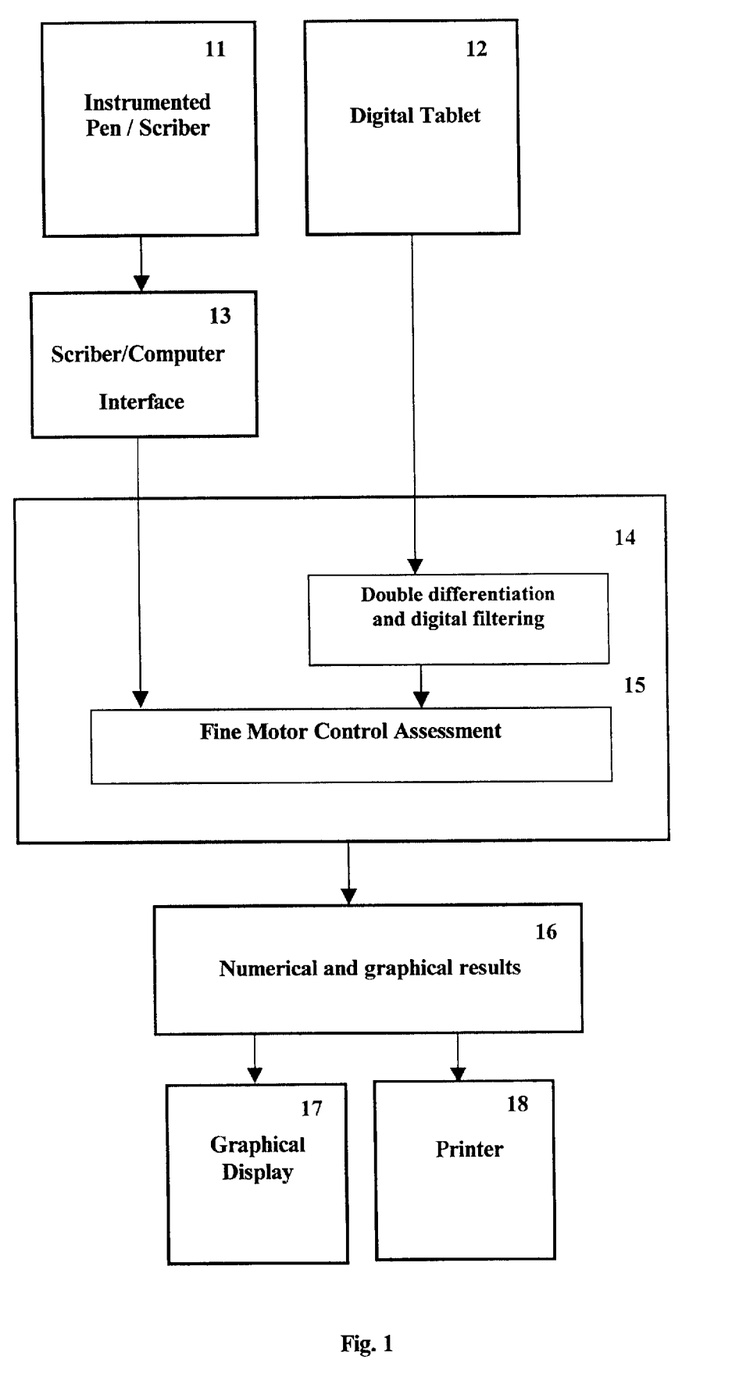
FIG. 1 is a schematic diagram showing the elements of the fine motor control assessment system of the present invention. The system includes means of producing numerical results and of graphical display showing behavior of correlation function, smoothness and synchronization measures in time.

Referring now to FIG. 1, let:

$w_1$ be a window on one of the compared signals;

w-step$_i$ be a window step (a parameter);

$sh_i$ be a shadow of window, $w_i$ on another compared signal.

Then the criteria, $Cr_2$ and $Cr_3$ are defined as follows:
Criterion II

The first order differences are defined as follows: sh-shift$_i$=(sh$_{i+1-shi}$)−(w$_{i+1}$−w$_i$) Based on sh-shift values for all windows under consideration, their distribution is built for a given axis. The percentage of all sh-shifts that are within 1, 2, or 3 sigma interval defines Criterion II for a given axis for a predetermined sigma interval.
Criterion III Given a pair of axes X and Y, Criterion III is defined as follows:

1. Synchronization between shifts on X and Y for window$_i$ Sync$_i$(xy)=sh-shift$_i$(x)−sh-shift$_i$(y)

2. Based on Sync values, the distribution is built and the standard deviation (sigma) is defined.

Figure 2:
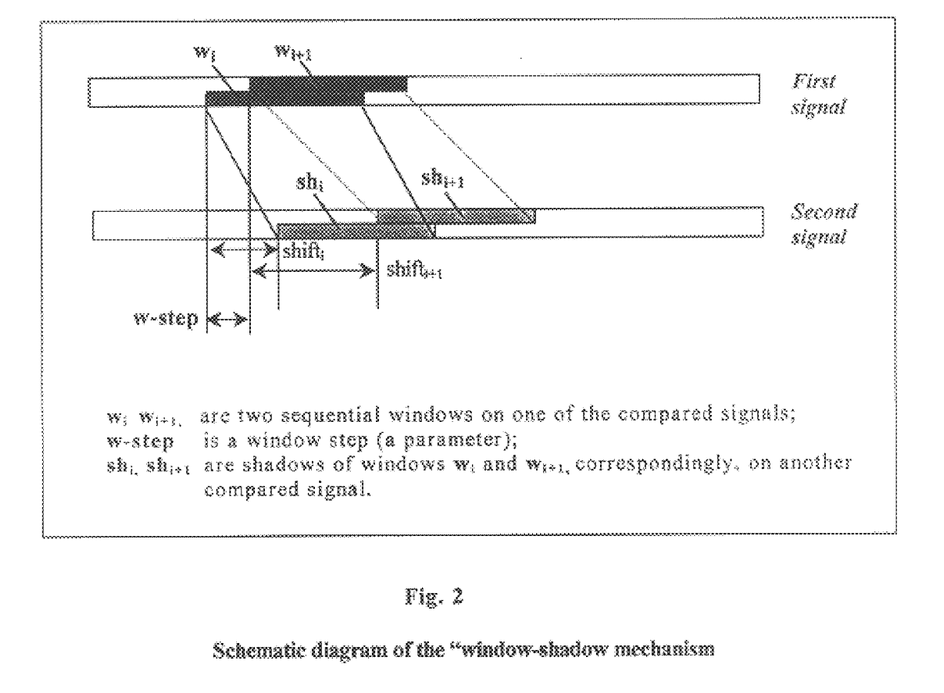
FIG. 2 is a schematic diagram showing the "window-shadow" mechanism used for identification of phase distortions between elementary (atomic) movements, or biological quanta.
Figure 3:
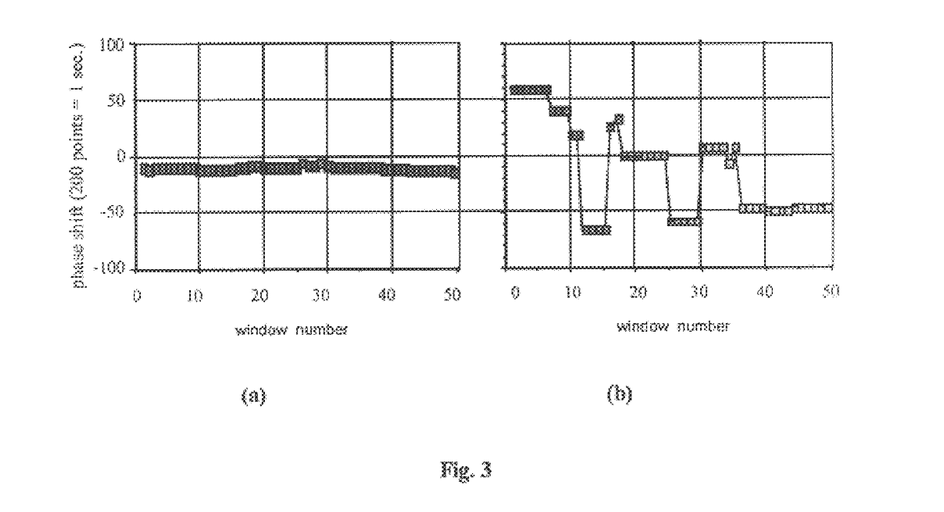
Figure 4A:
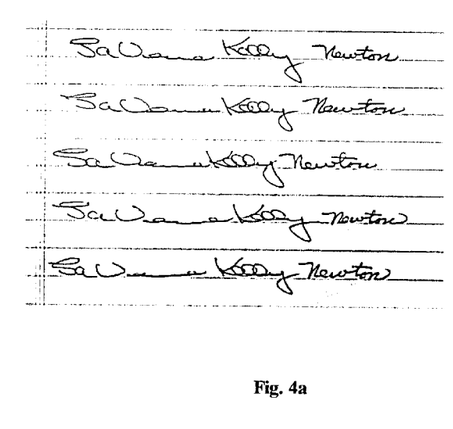
Figure 4B:
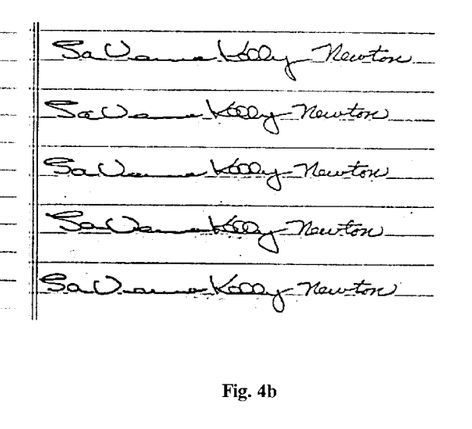

The smaller the value of sigma, the better synchronization of the handwriting motions. Criterion I that characterizes the repeatability of handwriting elementary strokes, combined with Criteria II and III that characterize the behavior of phase distortions between strokes, provide direct information about the subject's fine motor control functioning, and can be used as a powerful tool to convey an early indication of the subject's fine motor control deterioration.
Relevant experience
Experiments with Parkinson's Disease Patients The prototype of the system was created and used in experiments with Parkinson's disease patients. The tests demonstrated remarkably consistent changes in the measurements. The results have shown, for example, that while for a healthy person phase delays are represented by a smooth curve, for a person with neurological disorders, delays change in appearance fundamentally and are represented by a very oscillating graphs, as we can see on FIGS. 2 a and b, respectively.

The system not only accurately measures changes in fine motor control in the cases when we can observe visual differences in writing symbols, but, impressively, it gives an accurate assessment of the deterioration of handwriting dynamics when such is not evident from visual examination (see FIGS. 3, a and b) that show the signatures of a Parkinson's disease patient, Stage I, before and after taking medication. While the patient does not exhibit any essential differences in the pictorial representation of the handwriting samples, the patient's dynamic characteristics measured by the system changed essentially, they improved dramatically 40 min after taking L-dopa medication. The Correlation Function Criteria increased from 62.4% to 75,5%, and the Smoothness Criterion increased from 76.2% to 92.9% (see FIGS. 4, *a* and *b*).

Figure 5A:
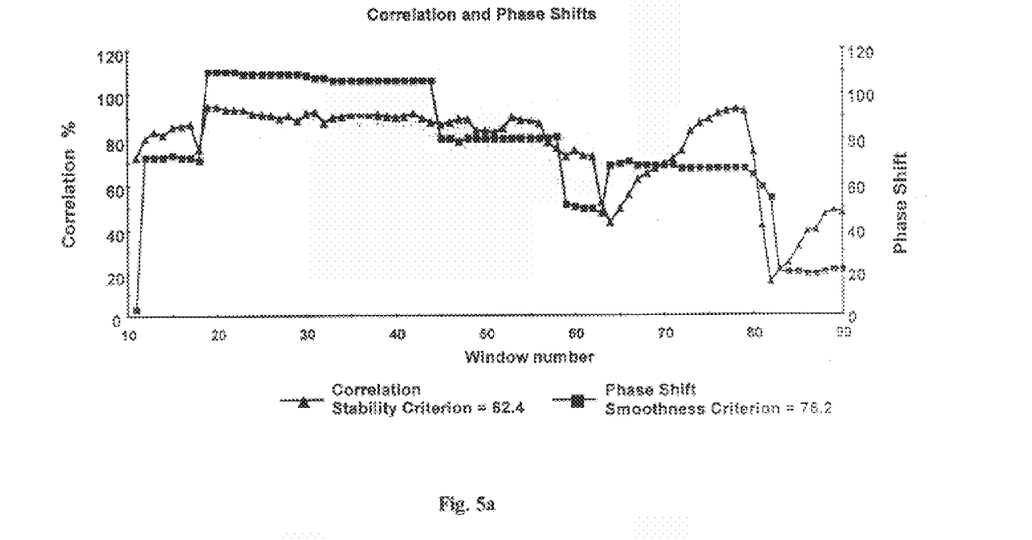
Figure 5B:
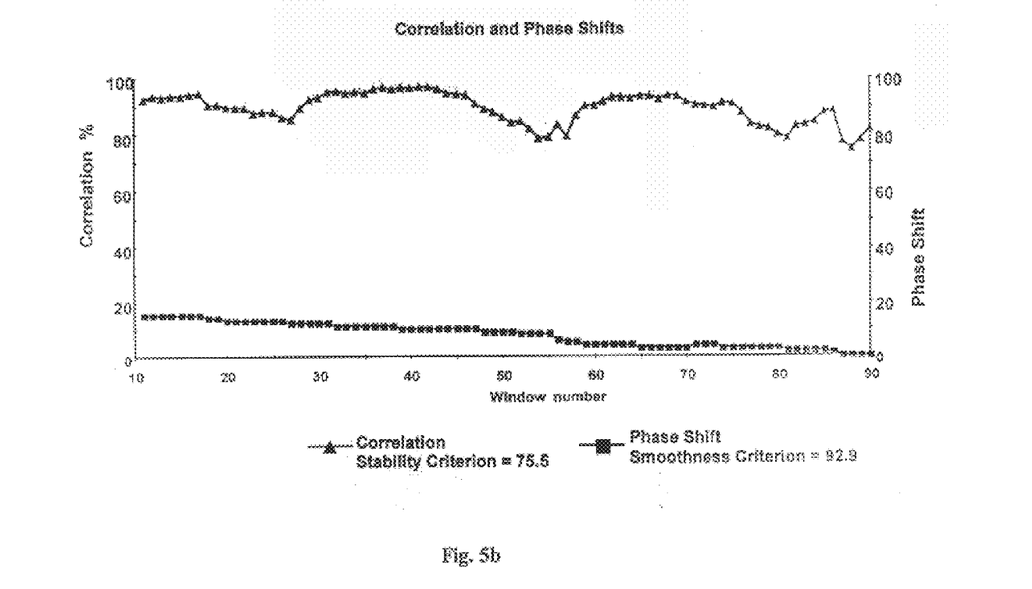
Figure 6A:
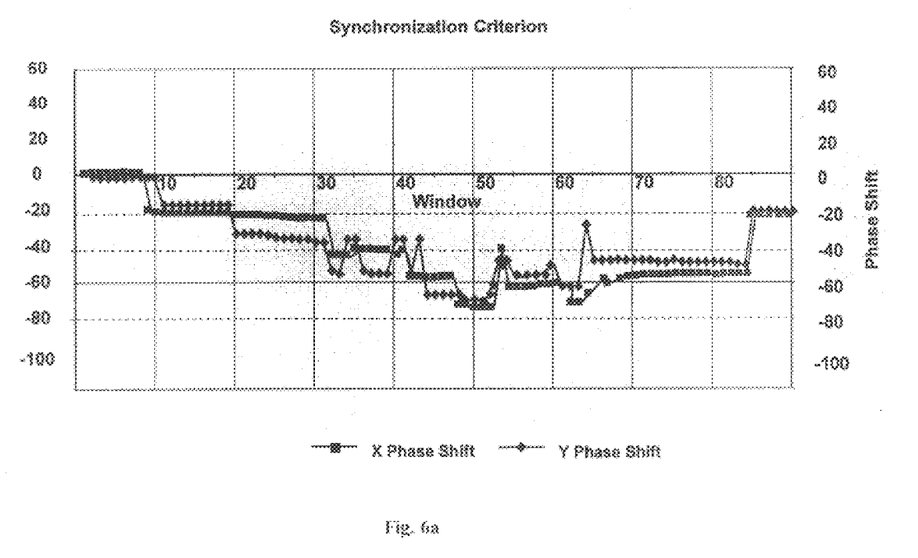
Figure 6B:
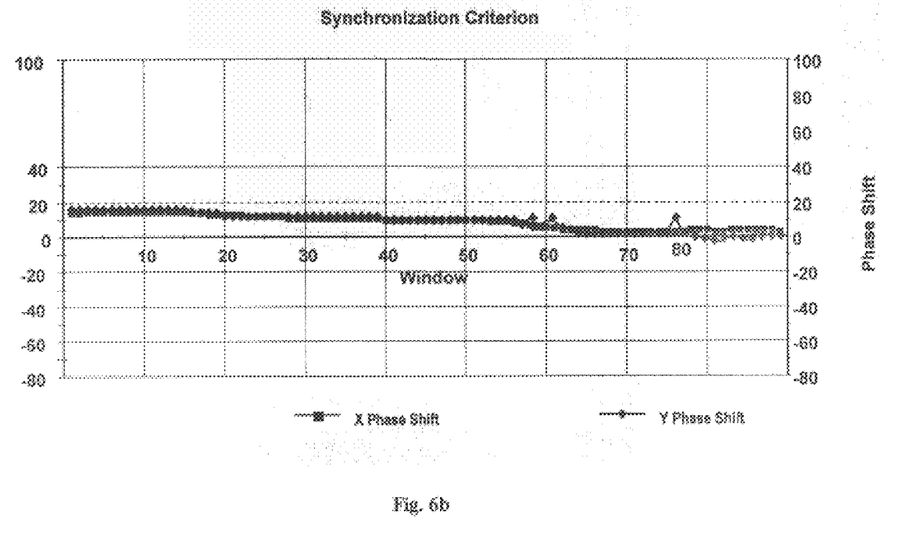

In order to illustrate the sensitivity of the system for assessment of synchronization of the motions, we present on FIG. 5 graphs of window-shadow shifts variations along X and Y axes for the same PD patient, stage I, before (5,*a*) and after L-dopa medication is taken (5,*b*). It is easy to see essential differences in the phase shift behavior along X-axis and Y-axis even at this early stage of the disease, and the positive effect of the medication when the shift behavior along X and Y become well synchronized. Based on the comparison of those shift variations, Criterion III is determined.

Importance of the New Solution

There are many clinical and non-clinical situations that call for a rapid, reliable and low-cost assessment of neurological function. It is also evident from the literature that the influence of neuro-toxic agents and other environmental factors on brain cells starts much earlier than it can be noticed by behavioral observations. At the very beginning of such a process, the fine motor skill disorder manifestation, lasting probably only milliseconds, could be measured if we had the necessary channels of biomedical information available. Such new channels of motor skill information might be explored by precise measurement and analysis of handwriting dynamics with use of the method of the present invention.

The device can be used for instantaneous analysis of handwriting dynamics. The information is collected on the spot and requires several (usually five) samples of handwriting. The analysis takes about a minute to return the criteria of stability, smoothness and synchronization of a person's handwriting movements. The method can be used an early detection and monitoring of fine motor skill disturbances.

Physical Implementation and Use of the System

The system can have two alternative configurations:

1. Configuration with an instrumented pen.

The system consists of an instrumented pen, which is attached to a parallel port of a PC, and accompanying software that implements the dynamic signal analysis and displays the results. The instrumented pen looks like ordinary one, but contains tiny sensors. The pen's motor sensing electronics consists of accelerometers that measure motions along the X and Y-axes, and a force cell that measures dynamics along the pen body.

The pen is easily connected to a PC by a light and flexible cable to a parallel connector, such as that normally used for a printer. Alternatively, the pen could communicate with a PC by means of infrared or RF transmitters. Installation of the pen is as easy as adding a "mouse" to a computer. Any personal computer as well as portable computers, such as Dell Inspiron of 12×9×1.7" size, 6.4 lb weight, can be used in the system.

2. Configuration with a Digitized grid

The method can be also implemented with the use of a sensitive digitizing tablet, or grid, combined with a simple non-instrumented stylus. A digitized tablet was used with the dimensions 9.6"×8.6" and thickness of 2", data rate of 460 points per second, 256 pressure levels, and resolution of 2540 lines per inch.

The analog signals of acceleration, pressure, or other dynamics, are sampled 200 times per second and are converted into a digital bit stream representing up to 1000 data points. Such a sampling rate satisfies the Nyquist criteria being applied to the handwriting signals. The power spectrum analysis performed on the signals produced with use of the instrumented pen showed that the highest frequency does not exceed 60 Hz. Thus, by using a 200 Hz sampling rate we comply with the ratio of 2.5–3.0 between the sampling rate and the highest harmonics of the processed signals recommended for practical applications.

The software is compatible with all common computers, and would not interfere with other uses of the computer. The software is written in C, C++languages, following a highly modular design.

A differentiation module is added to the software in the grid configuration in order to translate the initial signals of a stylus displacement into signals of acceleration in time.

Using an instrumented pen, a person may write on any surface, including regular paper, without any restrictions for a position of the writer or for orientation of the writing surface or location of that surface whereon the symbols are written. Using a digitized grid, a person is writing on the active area of the grid, for example, 6.4"×4.2" in our experiments, without restrictions for orientation. The method is absolutely not invasive; it does not require anything to be attached to the subject's body: neither sensor, nor wire. The device can be used for instantaneous analysis of handwriting dynamics giving an indication of the presence and extent of fine motor control deterioration. The information is collected on the spot and requires several, commonly five, samples of handwriting samples. The analysis takes less than a minute to return the numerical scores and graphical displays for criteria of stability, smoothness and synchronization of a person's handwriting movements. No special knowledge is required to operate the device. The subject is led through the test by a user-friendly interactive computer display.

One demonstration of the device and short written instructions will provide the individual all necessary information for a successful test.

Industrial Applications

The invention may find applications in the following medical areas:

monitoring patients with neurological disorders, such as Parkinson's Disease, for determination of the patient response to treatment;

early detection of fine motor impairment in at-risk populations;

monitoring of the effects of medications over time;

expediting clinical trials of neurological pharmaceuticals;

monitoring people with alcohol/drug abuse problems;

identification of the person's high risk factors to develop alcoholism;

detection of fine motor control deterioration as a result of exposure to toxic environmental materials;

research of mechanisms of intoxication of any kind that causes fine motor control impairment;

testing the efficacy of countermeasures to improve impaired fine motor functions.

It is therefore seen that the present invention to provides a rapid, reliable, and low-cost system for quantifying fine neuromuscular performance and fine motor control skills of human individuals using cursive writing and minimal equipment. In addition, the present invention provides a method for instantaneous, within the subject assessment of fine motor control with application of the correlation function analysis for comparison of behavioral random signals of handwriting dynamics, without the need to have reference data for that individual.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by-the prior art. Moreover, the invention as disclosed herein, may be suitably practiced in the absence of the specific elements that are disclosed herein.

The inventions in which an exclusive property or privilege is claimed are defined as follows:

1. A method for quantifying fine motor control of a human using analysis of cursive handwriting dynamics of a scriber on a writing surface, including the steps of:
   a. gathering a set of analog dynamic signals related to movement of a scriber, such analog dynamic signals being selected from the group-including analog dynamic signals of forces transmitted from a hand of the writer to a scriber, analog dynamic signals of scriber acceleration, analog dynamic signals of scriber velocity, and mixtures of such analog dynamic signals, along X and Y axes of a writing surface and measuring the dynamic signals along the axis of the scriber, as the Z axis, all said analog dynamic signals being measured as functions of time;
   b. converting the gathered analog dynamic signals from analog to digital form and processing or storing these digital signals in file;
   c. processing said digital signals by comparing and analyzing all combination pairs of the signals of the same nature taken from the file, utilizing the steps of:
      i. establishing mapping between phase coincident areas between two compared digital signals using a sliding window to find phase shift, or time distortion locations, wherein the sliding window is a piece of one signal, which is moved along the signal with a predetermined step of a size which is essentially less than the size of the window, and which is used to find for each window the corresponding piece in another signal of the pair on the basis of a position of maximum value of cross-correlation function between windows of one signal and the corresponding pieces of the other signal, called shadows, for determination of phase distortion, including time distortion, locations, each window being given an indicia;
      ii. eliminating phase shift distortions, including time distortions, between the two compared digital signals by the use of the mapping procedure of step (c.i.);
      iii. defining and storing the differences in positioning of each window and the shadow of each window by the indicia of that window computed for each axis;
      iv. differentiating the differences in positioning of each window and its shadows along one axis with the counterpart differences along another axis;
   d. means for determining similarity of the pair of signals using criterion $Cr_1$ with $Cr_2$ or $Cr_3$, or with both, combined;

wherein $Cr_1$ is determined by:
      i. performing cross-correlation analysis with evaluation of the maximum value of the corresponding cross-correlation function for each pair of x, y and z components of the digital signals;
      ii. producing a numerical score for criterion $Cr_1$;
   wherein $Cr_2$ is determined by:
      determining a portion of the first order differences for window-shadow shifts taken in a predetermined interval of the window-shadow shifts distribution defines $Cr_2$ for the corresponding axis, it characterizes smoothness of hand movement along this axis,
   wherein $Cr_3$ is determined by:
      determining the differences in positioning of windows and their shadows along one axis are compared with their counterparts along another axis, provided that the differences of shifts between a window and a shadow chosen for comparison axes yield to a normal distribution, let sigma denote a dispersion of the shift-differences distribution, then the portion of the differences between window-shadow shifts for two chosen axes taken within a predetermined interval defines $Cr_3$ for this pair of axes; and
   e. means of graphical display of correlation function between two compared signals, of variations of the phase shifts, or time distortions, and of variations of differences between phase distortion for two compared axes; whereby, fine motor control of the human operating the scriber is quantified.

2. The method of claim 1, wherein the sliding window method in step (c.i.) is used to find the position of maximum correlation functions between windows of one signal and the corresponding pieces of the other signal, called shadows, for determination of phase distortion locations.

3. The method of claim 1, wherein the sliding window in step (c.i.) is a piece of one signal called window, which is moved along the signal with a predetermined step of size which is essentially less than size of the window, and which is used to find for each window the corresponding piece in another signal of the pair on the basis of the position of maximum value of cross-correlation function between them.

4. Apparatus for assessment and monitoring of the fine motor control for quantifying measures of human neurological function, including:
   a. a scriber;
   b. means for gathering a set of analog dynamic signals related to movement. of the scriber during the process of cursive writing, such- analog dynamic signals being selected from the group consisting of forces transmitted from the hand of the writer to the scriber, scriber acceleration, scriber velocity, and mixtures thereof, along X and Y axes of a writing surface and measuring the dynamic signals along the axis of the scriber, as the Z axis, all signals being measured as functions of time;
   c. means for converting the analog dynamic signals from analog to digital form;
   d. means for processing or storing the resulting digital signals in file;
   e. means for providing a data pair composed of the digital data for analysis;
   f. means for processing the data pair of digital signals to eliminate phase shifts, or time distortions between them utilizing the steps of:
      i. establishing mapping between phase coincident areas between two compared digital signals using a sliding window to find phase shift, or time distortion locations, wherein the sliding window is a piece of one signal, which is moved along the signal with a predetermined step of a size which is essentially less than the size of the window, and which is used to find for each window the corresponding piece in another signal of the pair on the basis of the position of maximum value of cross-correlation function between windows of one signal and the corresponding pieces of the other signal, called shadows, for determination of phase distortion, including time distortion and locations, each window being given an indicia;

ii. eliminating phase shift distortions, including time distortions, between the two compared digital signals by the use of the mapping procedure of step (f.i.);

iii. defining and storing the differences in positioning of each window and the shadow of each window by the indicia of that window computed for each axis;

iv. differentiating the differences in positioning of each window and its shadows along one axis with the counterpart differences along another axis;

g. means for determining the similarity of the pair of signals using criterion $Cr_1$ with $Cr_2$ or $Cr_3$, or with both, combined, wherein $Cr_1$ is determined by:

i. performing cross-correlation analysis with evaluation of the maximum value of the corresponding cross-correlation function for each pair of x, y and z components of the digital signals;

ii. producing a numerical score for criterion $Cr_1$; wherein $Cr_2$ is determined by:

determining a portion of the first order differences for window-shadow shifts taken in a predetermined interval of the window-shadow shifts distribution defines $Cr_2$ for the corresponding axis, it characterizes smoothness of hand movement along this axis, wherein $Cr_3$ is determined by:

determining the differences in positioning of windows and their shadows along one axis are compared with their counterparts along another axis, provided that the differences of shifts between a window and a shadow chosen for comparison axes yield to a normal distribution, let sigma denote a dispersion of the shift-differences distribution, then the portion of the differences between window-shadow shifts for two chosen axes taken within a predetermined interval defines $Cr_3$ for this pair of axes;

h. means of graphical display of correlation function between two compared signals, of variations of the phase shifts, or time distortion, and of variations of differences between phase distortion for two compared axes; whereby fine motor control of a human operating the scriber is quantified.

5. The apparatus of claim 4, further including means for showing correlation function, smoothness and synchronization measures in time of an individual as compared to the general population, giving the maximum, mean, and standard deviation for each measure.

6. The apparatus of claim 5, further including means for showing the numerical results for the criteria of fine motor control analysis.

7. The apparatus of claim 6 wherein said means for showing the numerical results provide a machine display.

8. The apparatus of claim 6 wherein said means for showing the numerical results provide a printed message.

9. Apparatus for assessment and monitoring of the fine motor control for quantifying measures of human neurological function of a person, including:

a. a digitized writing surface for receiving non-instrumented scriber;

b. means for providing a data pair composed of the digital data for analysis;

c. means for differentiation of the signals of displacement produced by 5(b);

d, means for processing the data pair of digital signals to eliminate phase shifts, or time distortions between them utilizing the steps of:

i. establishing a mapping between phase coincident areas between two compared digital signals using a sliding window to find phase shift, or time distortion, locations, wherein the sliding window is a piece of one signal, which is moved along the signal with a predetermined step of a size which is essentially less than the size of the window, and which is used to find for each window the corresponding piece in another signal of the pair on the basis of the position of maximum value of cross-correlation function between windows of one signal and the corresponding pieces of the other signal, called shadows, for determination of phase distortion including time distortion and locations;

ii. eliminating phase shift distortions, including time distortions, between the two compared digital signals by the use of the mapping procedure of step (c.i.);

iii. defining and storing the differences in positioning of windows and their shadows by the window-number, being computed for each axis;

iv. differentiating differences in positioning of windows and their shadows along one axis with the counterpart differences along another axis;

e. means for determining similarity of the pair of signals using criterion $Cr_1$ with $Cr_2$ or $Cr_3$, or with both, combined, wherein $Cr_1$ is determined by:

i. performing cross-correlation analysis with evaluation of the maximum value of the corresponding cross-correlation function for each pair of x, y and z components of digital signals;

ii. producing a numerical score for criterion $Cr_1$; wherein $Cr_2$ is determined by:

determining a portion of the first order differences for window-shadow shifts taken in a predetermined interval of the window-shadow shifts distribution defines $Cr_2$ for the corresponding axis characterizes smoothness of hand movement along this axis, wherein $Cr_3$ is determined by:

determining the differences in positioning of windows and their shadows along one axis are compared with their counterparts along another axis, provided that the differences of shifts between a window and a shadow chosen for comparison axes yield to a normal distribution, let sigma denote a dispersion of the shift-differences distribution, then the portion of the differences between window-shadow shifts for two chosen axes taken within a predetermined interval defines $Cr_3$ for this pair of axes; and f. means of graphical display of correlation function between two compared signals, of variations of the phase shifts, or time distortion, and of variations of differences between phase distortion for two compared axes; whereby fine motor control of the person writing on the digitized writing surface is quantified.

10. The apparatus of claim 9, further including means for showing correlation function, smoothness and synchronization measures in time of an individual as compared to the general population, giving the maximum, mean, and standard deviation for each measure.

* * * * *